US00PP24369P2

(12) United States Plant Patent
Hurkman

(10) Patent No.: US PP24,369 P2
(45) Date of Patent: Apr. 1, 2014

(54) ***PETUNIA* PLANT NAMED 'BALSPUNURST'**

(50) Latin Name: *Petunia×hybrida*
Varietal Denomination: Balspunurst

(75) Inventor: Margaret Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 86 days.

(21) Appl. No.: 13/507,858

(22) Filed: Aug. 2, 2012

(51) Int. Cl.
*A01H 5/00* (2006.01)

(52) U.S. Cl.
USPC ..... Plt./356.13; Plt./356.1; Plt./356.18

(58) Field of Classification Search
USPC ..... Plt./356.1, 356.13, 356.18
See application file for complete search history.

*Primary Examiner* — Susan McCormick Ewoldt
(74) *Attorney, Agent, or Firm* — Audrey Charles

(57) ABSTRACT

A new and distinct cultivar of *Petunia* plant named 'Balspunurst', characterized by its purple and white star-patterned bicolored flowers, medium green-colored foliage, and compact, upright-mounded growth habit, is disclosed.

1 Drawing Sheet

Latin name of genus and species of plant claimed: *Petunia× hybrida.*

Variety denomination: 'Balspunurst'.

BACKGROUND OF THE INVENTION

The present invention relates to a new and distinct cultivar of *Petunia* plant botanically known as *Petunia×hybrida* and hereinafter referred to by the cultivar name 'Balspunurst'.

The new cultivar originated in a controlled breeding program in Arroyo Grande, Calif. during February 2009. The objective of the breeding program was the development of *Petunia* cultivars with single type flowers, unique flower coloration, and compact, upright-mounded growth habit.

The new *Petunia* cultivar was the result of a self-pollination of the proprietary *Petunia×hybrida* breeding selection coded 5879-4, not patented, characterized by its violet-blue and white bicolored flowers, medium green-colored foliage, and moderately vigorous, compact, upright-mounded growth habit. The new cultivar was discovered and selected as a single flowering plant within the progeny of the above stated self-pollination during June 2009 in a controlled environment in Arroyo Grande, Calif.

Asexual reproduction of the new cultivar by terminal stem cuttings June 2009 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspunurst' as a new and distinct cultivar of *Petunia* plant:

1. Purple and white star-patterned bicolored flowers;
2. Medium green-colored foliage; and
3. Compact, upright-mounded growth habit.

Plants of the new cultivar differ from plants of the parent primarily in having more of a purple flower color and a more distinct star-shaped pattern.

Of the many commercially available *Petunia* cultivars, the most similar in comparison to the new cultivar is Cascadias Bicolor Purple 'Dancasbipur', not patented. However, in comparison, plants of the new cultivar differ from plants of 'Dancasbipur' in at least the following characteristics:

1. Plants of the new cultivar have a flower color different from plants of 'Dancasbipur'; and
2. Plants of the new cultivar have a growth habit that is more compact than plants of 'Dancasbipur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balspunurst'. The plants were grown in 4-inch pots for 6 weeks in a greenhouse in West Chicago, Ill.

DETAILED BOTANICAL DESCRIPTION

Figure 1:
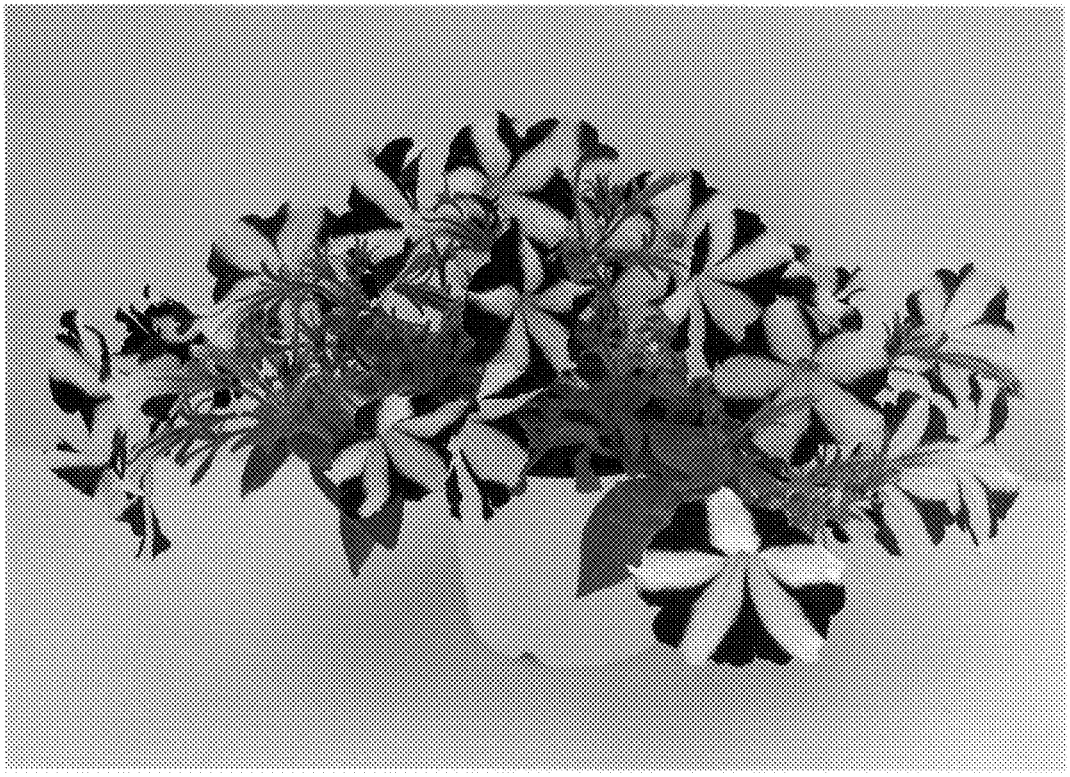
FIG. 1 illustrates a side view of the overall growth and flowering habit of 'Balspunurst'.
Figure 2:
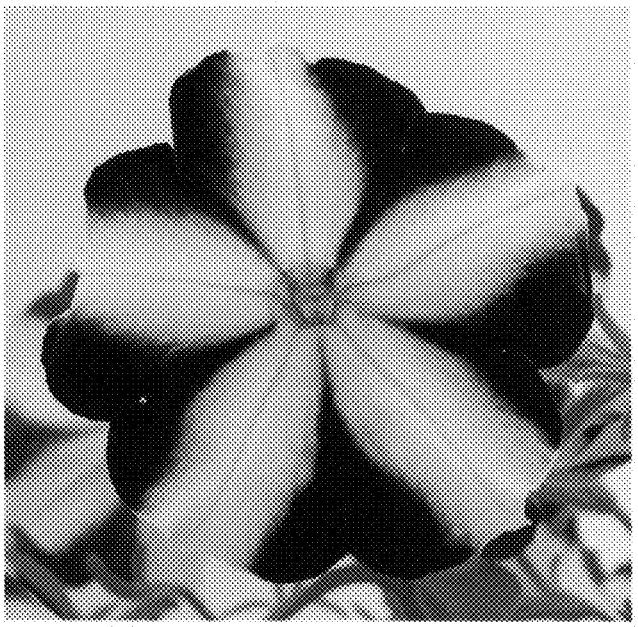
FIG. 2 illustrates a close-up view of an individual flower of 'Balspunurst'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Balspunurst.

Parentage:

*Female and male parents*.—Proprietary *Petunia×hybrida* breeding selection coded 5879-4, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching

Plant description:

*Commercial crop time*.—Approximately 6 to 8 weeks from a rooted cutting to finish in a 10 cm pot.

*Growth habit and general appearance*.—Moderately vigorous, compact, upright-mounded.

*Size*.—Height from soil level to top of plant plane: Approximately 11.8 cm. Width: Approximately 32.4 cm.

*Branching habit*.—Freely branching, pinching improves basal branching Quantity of main branches per plant: Approximately 4.

*Branch*.—Strength: Moderate. Length: Approximately 14.4 cm. Diameter: Approximately 3.0 mm. Length of central internode: Approximately 2.1 cm. Texture: Densely glandular pubescent with a mixture of long and short hairs. Gland color: Colorless. Color of young and mature stems: 144A.

Foliage description:

*General description*.—Quantity of leaves per main branch: Approximately 9. Fragrance: Slight. Form: Simple. Arrangement on flowering stem: Opposite.

*Leaves*.—Aspect: Acute angle to stem. Shape: Ovate to elliptic. Margin: Entire. Apex: Acute. Base: Attenuate. Venation pattern: Pinnate. Length of mature leaf: Approximately 4.7 cm. Width of mature leaf: Approximately 3.0 cm. Texture of upper surface: Sparsely glandular pubescent. Texture of lower surface: Moderately glandular pubescent. Gland color: Colorless. Color of upper surface of young foliage: 137A with venation of 144B to indistinguishable. Color of lower surface of young and mature foliage: 138B with venation of 144B to indistinguishable. Color of upper surface of mature foliage: 137B with venation of 144B to indistinguishable.

*Petiole*.—Length: Approximately 3.0 mm. Width: Approximately 3.0 mm. Texture: Densely glandular pubescent with a mixture of long and short hairs. Gland color: Colorless. Color: 144B.

Flowering description:

*Flowering habit*.—'Balspunurst' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 19. Fragrance: Slight.

*Bud*.—Rate of opening: Generally takes 2 to 3 days for bud to progress from first color to fully open flower. Quantity per plant: Approximately 6.

*Bud just before opening*.—Shape: Oblong. Length: Approximately 4.0 cm. Diameter at apex: Approximately 6.0 mm. Diameter at base: Approximately 3.0 mm. Texture: Densely glandular pubescent. Gland color: Colorless. Color of petals: 79B and NN155B. Color of tube: 79B with venation of 145A.

*Corolla*.—Diameter: Approximately 6.5 cm.

*Petals*.—Quantity: 5, fused to form a tube. Shape: Obovate. Appearance: Velvety. Margin: Entire, slightly wavy. Apex: Acute. Length from tube: Approximately 3.1 cm. Length of free portion: Approximately 1.5 cm. Width: Approximately 3.2 cm. Texture of upper surface: Glabrous. Texture of lower surface: Sparsely glandular pubescent. Gland color: Colorless. Color of upper surface when first and fully open: 79A with centers of NN155D bordered with an overlay of N81A, midveins of 145B. Color of lower surface when first and fully open: 79C with centers of NN155D and miviens of 145A.

*Corolla tube*.—Length: Approximately 3.1 cm. Diameter at distal end: Approximately 9.0 mm. Diameter at proximal end: Approximately 3.0 mm. Texture of inner surface: Glabrous. Texture of outer surface: Densely glandular pubescent. Gland color: Colorless. Color of inner surface: NN155A with stripes of 79B to 79D and venation of 145A. Color of outer surface: 79B with venation of 145A.

*Sepals*.—Quantity per flower: 5, fused at base. Shape: Linear. Apex: Acute. Length: Approximately 1.8 cm. Width: Approximately 2.5 mm. Texture of upper and lower surfaces: Densely glandular pubescent. Gland color: Colorless. Color of upper surface: 137A. Color of lower surface: 137B transitioning to 144B at base.

*Peduncle*.—Strength: Strong. Aspect: Acute angle to stem. Length: Approximately 2.6 cm. Diameter: Approximately 2.0 mm. Texture: Densely glandular pubescent with a mixture of long and short hairs. Gland color: Colorless. Color: 144A with an overlay of 187A.

*Reproductive organs*.—Androecium: Stamen quantity: 5, basifixed. Stamen length: Approximately 2.3 cm. Filament length of fixed portion: Approximately 8.0 mm. Filament color: NN155D with an overlay of 79C. Anther shape: Bilobed. Anther length: Approximately 1.0 mm. Anther color: 155A. Pollen amount: Abundant. Pollen color: 155D. Gynoecium: Pistil quantity: 1 per flower. Pistil length: Approximately 2.6 cm. Stigma shape: Funnel. Stigma length: Approximately 2.0 mm. Stigma color: 144A. Style length: Approximately 2.1 cm. Style color: 145B. Ovary length: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balspunurst', substantially as herein shown and described.

* * * * *